(12) United States Patent
Sargent

(10) Patent No.: US 6,260,551 B1
(45) Date of Patent: Jul. 17, 2001

(54) POST MORTEM ADJUSTABLE MANDIBULAR MAXILLARY LOCK

(76) Inventor: Roger E. Sargent, 256 Prospect St., Franklin, NH (US) 03235-1970

( * ) Notice: Subject to any disclaimer, the term of this patent is extended or adjusted under 35 U.S.C. 154(b) by 0 days.

(21) Appl. No.: 09/597,104

(22) Filed: Jun. 20, 2000

(51) Int. Cl.[7] .................................................. A61F 5/56
(52) U.S. Cl. ............................ 128/848; 128/859; 27/27.1
(58) Field of Search .................................. 128/846, 848, 128/859–862; 27/1, 21.1

(56) References Cited

U.S. PATENT DOCUMENTS

| | | | |
|---|---|---|---|
| 1,870,566 | * | 8/1932 | Heitritter ............................ 27/21.1 |
| 2,172,252 | * | 9/1939 | Moore ............................... 27/21.1 |
| 3,103,052 | * | 9/1963 | Rector ............................... 27/21.1 |
| 5,443,482 | * | 8/1995 | Stone .................................. 606/73 |

* cited by examiner

Primary Examiner—Michael A. Brown
(74) Attorney, Agent, or Firm—William B. Ritchie

(57) ABSTRACT

A post-mortem adjustable mandibular/maxillary lock. The apparatus permits easily position on a cadaver, even ones that have jaw problems such as dentures, diseased bones, brittle bones, trauma as well as deceased having normal teeth and bones. The apparatus locks the jaws bones in a correct anatomical position during the embalming process and provides a natural mouth closure appearance of the remains for viewing by the bereaved during the funeral ceremony.

3 Claims, 2 Drawing Sheets

POST MORTEM ADJUSTABLE MANDIBULAR MAXILLARY LOCK

FIELD OF THE INVENTION

The invention relates to the field of embalming aids and appliances, in particular, an adjustable apparatus for the holding the jawbones of a deceased in a correct anatomical position during the embalming process and to provide a natural mouth closure appearance of the remains.

BACKGROUND OF THE INVENTION

When the relatives decide upon the funeral proceedings and determine that the body is to be exposed, it is the responsibility of the embalmer to make certain that the preservation of the appearance of the body of the deceased is as natural looking as possible. The traditional method used to accomplish this task consists of wiring the maxillary bone, that is the upper jawbone, to the mandible, the lower jawbone. The use of wiring methods is dependent upon the existence of bone structure that would support such use.

Another option is the use of a mandible suture. This method is used when the lower jaw tissue has undergone degeneration due to disease or trauma. A suture is inserted between the lower lip and gum and brought out at a point just behind the chin and then the needle is reinserted into the same hole and brought up behind the mandible through the floor of the mouth just beneath the tip of the tongue. The upper portion of the suture is then attached to the upper jaw to complete the suture. This method is difficult to use and has the added problem of distorting the appearance of the lips.

In cases where the deceased has died of the result of trauma resulting in disfigurement of the face or jaw or where the deceased has experienced substantial bone loss or disease, proper mouth closure is difficult if not impossible to obtain with current methods. There is not found in the prior art a reliable, easily insertable apparatus that permits adjustment to readily achieve a correct anatomical position and provides a natural mouth closure.

SUMMARY OF THE INVENTION

The invention is a post-mortem adjustable mouth closing apparatus for a cadaver. A first member that is permanently attached to the mandible of the cadaver is provided. A second member that is also permanently attached to the maxillary bone of the cadaver is similarly provided. The first member is adjustably engageable with the second member wherein the anatomical position of the two bones can be positioned substantially anatomically correct. Further, a substantially life-like mouth closure can be locked into position. The first and second members are attached to the respective bones of the cadaver by self-tapping screws.

Therefore, it is an aspect of the invention to provide a post-mortem adjustable mandibular/maxillary lock that is easily attached to a cadaver's jawbone.

Another aspect of the invention is to provide a post-mortem adjustable mandibular/maxillary lock that can provide a substantially natural and anatomically correct position of the mouth closure.

Still another aspect of the invention is to provide a post-mortem adjustable mandibular/maxillary lock that is easily adjustable.

It is an aspect of the invention is to provide a post-mortem adjustable mandibular/maxillary lock that can be screwed into position.

Another aspect of the invention is to provide a post-mortem adjustable mandibular/maxillary lock that can be inexpensively manufactured.

Finally, it is an aspect of the invention is to provide a post-mortem adjustable mandibular/maxillary lock that can be used on a cadaver that has suffered face trauma or jawbone degeneration or loss.

DETAILED DESCRIPTION OF THE INVENTION

As noted above, the process of embalming uses techniques and methods that tend to recreate or simulate the natural features of the deceased for the purpose of presenting the deceased at funeral ceremonies. It is important then that the jawbones are in a correct anatomical position and that a natural appearance be maintained so that the bereaved can be view their loved one and remember him/her as he/she looked in life. This invention has been created for the purpose of overcoming the limitations and shortcomings of prior techniques and thus accomplishes the purpose of natural mouth closure appearance in a simpler and more efficient manner than previously possible.

Figure 1:
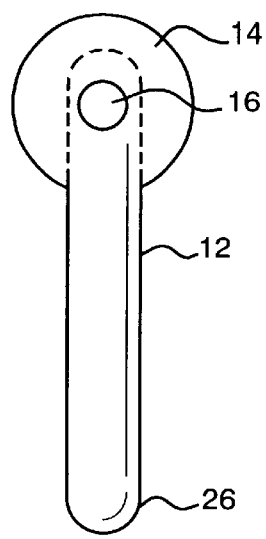
FIG. 1 is a front view of the mandibular member in accordance with the invention.
Figure 4:
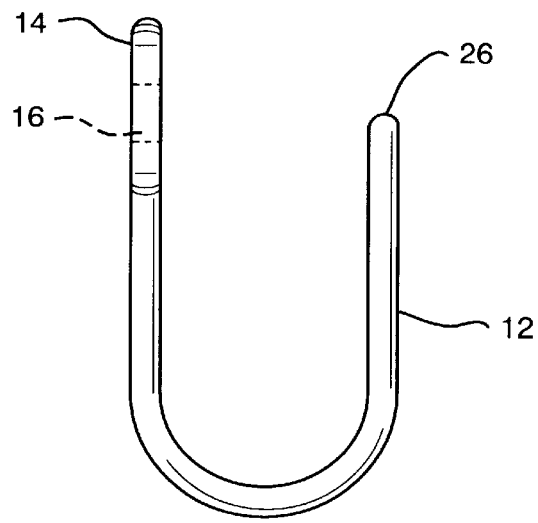
FIG. 4 is a side view of the mandibular member.

As shown in FIGS. 1 and 4, mandibular member 12 is used to attach invention 10 to a deceased's lower jaw. Opening 16 is at one end. Screw 18, which is preferably a #6 by ½ inch self-drilling bone penetrating screw or similar fastening device. As noted, member 12 is substantially u-shaped so that length between opening 16 and opening 20 (shown in FIG. 2) can be easily adjusted.

Mandibular member 12 comprises head 14 which is preferably about 5/16 inches in diameter with opening 16 which is preferably about 3/16 inches in diameter. Member 12 is secured to the mandible by screw 18 directly into the mandible at a mid-line below the lower frontal incisor's roots. The tab 26 is preferably rounded to prevent the user from injury. The overall length is about 1¾ inches long and ¼ inch wide. However, these dimensions are not critical.

Figure 2:
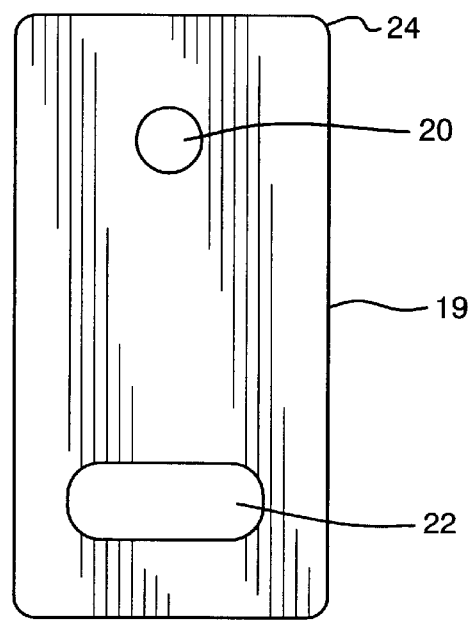
FIG. 2 is a front view of the maxillary member in accordance with the invention.
Figure 3:
FIG. 3 is detailed view of a typical screw used to lock the invention in place on remains of the deceased.

As shown in FIG. 2, maxillary member 19 is preferably rectangular shaped with ends rounded as with the mandibular member 12. Maxillary member 19 is securely fastened to the cadaver's maxillary bone above the dental line. Member 19 is securely fastened to the cadaver's maxillary bone at a mid-line point above the upper frontal incisor's roots. The overall size is preferably about ¾ inch long and a ½ inches wide. Slot 22 is dimensioned so that tab 26 can easily inserted therethrough so that the two members can engage one another to permit easy adjustment of the invention 10. Opening 20 is sized similar to opening 16 so that a screw 18 may be used to secure this member to the deceased's mandible.

Once the screws 18 penetrate the bones and secure members 12 and 19 in place, tab 26 passes through slot 22. The adjustment is accomplished by bending tab 26 to create the desired tension of teeth or dentures together. If teeth or dentures are absent, the adjustment occurs when the embalmer will create a natural appearance by positioning the jawbones in the position that is felt would be correct if the deceased did have teeth. As everyone's length of teeth is different, the space between gum lines will vary accordingly. The adjustment is done by trial and error and observing the mouth closure and lip appearance. As it may require 3 or 4 adjustments of tab 26 until the right length is achieved, it is important that tab 26 can be easily bent at different locations along its length.

In the preferred embodiment, the invention is made of 0.010" thick soft annealed steel in bright #2 finish. This material is preferred because tab 26 can be easily bent and then cut to length using scissors. In this manner, any extra portion of tab 26 can be easily removed.

Figure 5:
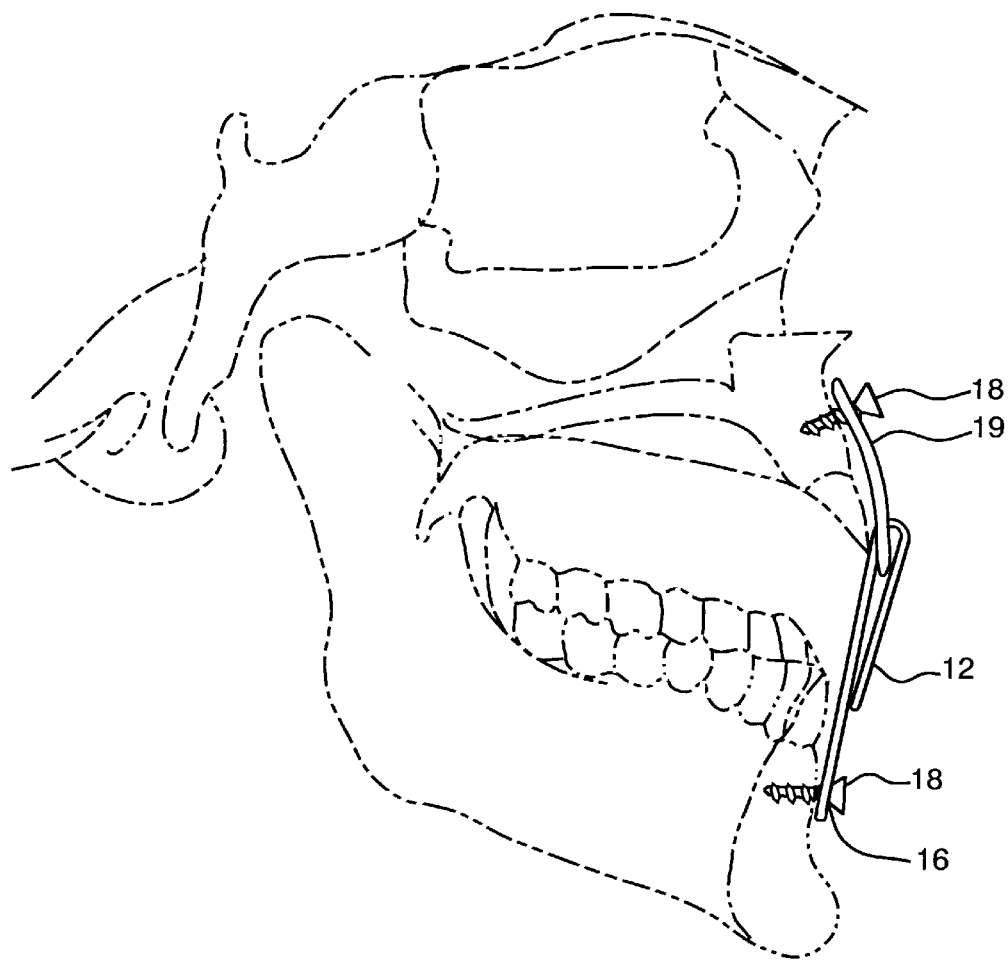
FIG. 5 is an illustration of the invention positioned on the jawbone of a cadaver.

FIG. 5 is an illustration of the invention position on the jaw. Note that the mouth closure is easily adjusted as described above.

While there have been described what are at present considered to be the preferred embodiments of this invention, it will be obvious to those skilled in the art that various changes and modifications may be made therein without departing from the invention and it is, therefore, aimed to cover all such changes and modifications as fall within the true spirit and scope of the invention.

What is claimed is:

1. A post-mortem adjustable mouth closing apparatus for a cadaver comprising:

a first member that is permanently attached to the mandible of the cadaver;

a second member that is permanently attached to the maxillary bone of the cadaver such that said first member is adjustably engageable with said second member wherein the anatomical position of the two bones can be positioned substantially anatomically correct and a substantially life-like mouth closure can be locked into position;

wherein said first member is attached to said second member by folding one of said members to form a substantially u-shaped band and then inserting said member through a slot in the other of said members wherein a distance between the respective points of attachment of said members can be provided that positions the cadaver's mandible relative to the maxillary bone.

2. The post-mortem adjustable mouth closing apparatus of claim 1 wherein said first member is substantially flat and rectangular having a width and a slot and wherein said second member is also substantially flat and rectangular having a width and length such that the length is substantially greater than the length and such that the width of said second member is dimensioned to correspond to the slot of said first member.

3. The post-mortem adjustable mouth closing apparatus of claim 2 wherein said tab is made from a malleable metal such that said tab is easily bent and cut by hand.

\* \* \* \* \*